(12) United States Patent
Wunderink et al.

(10) Patent No.: US 6,866,999 B2
(45) Date of Patent: Mar. 15, 2005

(54) METHOD FOR IDENTIFYING INCREASED RISK OF DEATH FROM COMMUNITY ACQUIRED PNEUMONIA

(76) Inventors: Richard Glenn Wunderink, 8363 Barncliff Cove, Germantown, TN (US) 38139; Grant William Waterer, 3/13 Hayes Avenue, Yokine 6060 (AU)

( * ) Notice: Subject to any disclaimer, the term of this patent is extended or adjusted under 35 U.S.C. 154(b) by 136 days.

(21) Appl. No.: 09/973,850

(22) Filed: Oct. 10, 2001

(65) Prior Publication Data

US 2002/0086016 A1 Jul. 4, 2002

Related U.S. Application Data

(60) Provisional application No. 60/239,133, filed on Oct. 10, 2000.

(51) Int. Cl.[7] ............................ C12Q 1/68; C12P 19/34; C07H 21/02
(52) U.S. Cl. ........................ 435/6; 435/91.2; 536/23.1; 536/24.31; 536/24.33
(58) Field of Search .......................... 435/6, 91.2, 183; 536/23.1, 24.31, 24.33

(56) References Cited

U.S. PATENT DOCUMENTS

| | | | | |
|---|---|---|---|---|
| 5,200,313 | A | * | 4/1993 | Carrico ........................... 435/6 |
| 6,294,339 | B1 | * | 9/2001 | Wunderink et al. ............ 435/6 |
| 2002/0119455 | A1 | * | 8/2002 | Chan .............................. 435/6 |

FOREIGN PATENT DOCUMENTS

EP    0 200 362 A2    3/1986
EP    0 201 184 A2    3/1986

OTHER PUBLICATIONS

Zhang et al., Bioinformatics, vol. 19, No. 1, 2003, pp. 14–21.*
Fine et al., "A Prediction Rule to Identify Low–Risk Patients with Community Acquired Pneumonia", The New England Journal of Medicine 1997 336 (4):243–250.
Hirose et al., "The E–linked subregion of the major histocompatibility complex down–regulates autoimmunity in NZB X NZW $F_1$ mice", Immunogenetics 1994 40:150–153.
Wilson et al., "An Allelic Polymorphism within the Human Tumor Necrosis Factor α Promoter Region Is Strongly Associated with HLA A1, B8, and DR3 Alleles", J. Exp. Med. 1993 177:557–560.

* cited by examiner

Primary Examiner—Bradley L. Sisson
(74) Attorney, Agent, or Firm—Licata & Tyrrell P.C.

(57) ABSTRACT

This invention relates to diagnostic methods based upon a particular genotype in the Tumor Necrosis Factor (TNFα) gene, more specifically, an adenine and guanine ("GA") at the –308 site (or AA) rather than the GG at this locus. More specifically, this invention relates to a method for diagnosis of increased risk of death in patients with community-acquired pneumonia (CAP) and diagnosing pre-disposition or susceptibility to increased risk of death in patients who develop CAP, by screening for the presence of this polymorphism. The invention also relates to compositions for screening for the polymorphism and improved treatment choices for patients having the polymorphism of the present invention.

The invention also relates to screening assays and therapeutic and prophylactic methods.

1 Claim, No Drawings

METHOD FOR IDENTIFYING INCREASED RISK OF DEATH FROM COMMUNITY ACQUIRED PNEUMONIA

INTRODUCTION

This application claims the benefit of priority from U.S. provisional application Ser. No. 60/239,133 filed Oct. 10, 2000.

FIELD OF THE INVENTION

This invention relates to diagnostic methods based upon a particular genotype in the Tumor Necrosis Factor (TNFα) gene, more specifically, a guanine (G) to adenine (A) transition at the −308 site in one of the TNFα genes (SEQ ID NO:1) giving a GA (SEQ ID NO:2) (or adenine adenine genotype, AA (SEQ ID NO:3)) genotype rather than the GG genotype (SEQ ID NO:1) at this locus. More specifically, this invention relates to a method for diagnosis of increased risk of death in patients with community-acquired pneumonia (CAP) and diagnosing pre-disposition or susceptibility to increased risk of death in patients who develop CAP, by screening for the presence of this A allele risk polymorphism. The invention also relates to compositions for screening for the polymorphism and improved treatment choices for patients having the polymorphism of the present invention. The invention also relates to screening assays and therapeutic and prophylactic methods.

BACKGROUND OF THE INVENTION

Pneumonia is a common clinical entity, particularly among the elderly. A thorough understanding of the epidemiology and microbiology of community-acquired pneumonia (CAP) is essential for appropriate diagnosis and management. Although the microbiology of CAP has remained relatively stable over the last decade, there is new information on the incidence of atypical pathogens, particularly in patients not admitted to hospital, and new information on the incidence of pathogens in cases of severe CAP and in CAP in the elderly. Recent studies have provided new data on risk factors for mortality in CAP, which can assist the clinician in decisions about the need for hospital admission. The emergence of antimicrobial resistance in *Streptococcus pneumonia*, the organism responsible for most cases of CAP, has greatly affected the approach to therapy, especially in those patients who are treated empirically. Guidelines for the therapy of CAP have been published by the American Thoracic Society, the British Thoracic Society, and, most recently, the Infectious Diseases Society of America and others. These guidelines differ in their emphasis on empirical versus pathogenic-specific management.

CAP remains a significant health problem and patients continue to die despite receiving appropriate antibiotic therapy. Modification of the host immune response, both anti- and pro-inflammatory approaches, has yet to live up to the promise of improved outcome. Despite this, there is significant reason for optimism. Some immunomodulatory therapies clearly have efficacy in some patients. As the understanding of the immune response to pneumonia improves our ability to tailor specific therapies for individual patients will also improve, hopefully avoiding the deleterious effects that have so far prevented the development of an effective immune based therapy. The possibility of delivering cytokines directly to the lung, is a particularly promising way of achieving the desired pulmonary effect without systemic side effects. Corticosteroids are currently unique in that they have a proven role in the therapy of pneumonia due to *P. carinii*. The development of pathogen specific therapies, such as INF for *L. pneumophila*, based on an improved understanding of host-pathogen interactions, are awaited.

The past 20 years has seen an explosion in our knowledge of human immunology and we are only now beginning to explore the therapeutic possibilities this has made available. The next 10 years promises to finally provide a significant advance in the therapy of pneumonia, the first substantial gain since penicillin.

In light of the prevalence of CAP and the evolution of resistance in the most common bacterial CAP pathogen, physicians advise obtaining specimens for culture of CAP pathogens and analyzing patterns of susceptibility, especially of *S. pneumonia*, in their communities, using antibiotics appropriately and prudently, according to prevailing susceptibilities when empirical treatment is called for, and immunizing their susceptible patients with pneumococcal and influenza vaccines. This is because the mortality of patients with severe CAP approaches or may exceed 20%, compared to less than 1% for patients with non-severe CAP (Fine et al. *New. Engl. J. Med.* 1997.336:243–308, British Thoracic Society, *Q. J. Med.* 1987.239:192–220, Niederman et al. *Am. Rev. Resp. Dis.* 1993.148:1418–1426). In such cases an ability to improve accuracy of diagnosis of or predisposition or susceptibility to severe CAP would be of distinct advantage and may lead to improved outcomes and lower medical costs for such patients.

TNFα acts on many healthy cells in addition to cancer cells and has been widely described in the literature. See e.g., Alfonso et al., *Immunogenetics* 1994.39:150–154. See also, Wilson et al., *J. Exp. Med.* 1993.177:557–560. It is important in regulating immune and inflammatory response and plays a large role in septic shock. It is released by a variety of cells including red and white blood cells, cells that line blood vessels, nervous system cells, muscle cells, bone cells, and some tumor cells. Although it was first observed to kill certain tumor cells (sarcoma cells), TNF has been found to help some tumors grow. In addition, TNF can be very toxic to normal cells. Early experiments found that administering TNF caused fever and loss of appetite. TNF also has been shown to affect the metabolism of many cell types, causing them to need more oxygen. It has been found to play a role in many autoimmune diseases, such as rheumatoid arthritis and myasthenia gravis. Certain viral and bacterial infections can cause healthy cells to produce elevated levels of TNF. It is a surprising feature of the present invention to be able to identify patients having an increased risk of death from CAP by the method of the present invention thereby identifying more effective treatment options such as pneumococcal and influenza vaccination of such at risk patients.

BRIEF SUMMARY OF THE INVENTION

It is a particular object of the invention to provide a method of identifying predisposition or susceptibility to increased risk of death in patients with CAP. Thus, the invention also relates to compositions for screening for the TNFα A allele, i.e., GA or AA genotype at the −308 site and improved treatment choices for patients identified at being at risk for an increased risk of death from CAP. Subjects with a TNFα AA genotype at the −308 site are believed to be at a similar or greater risk of death than patients with the GA genotype. The invention also relates to screening assays using the TNFα A allele protein described herein and therapeutic and prophylactic methods discovered using such screening assays.

Other preferred embodiments of the present invention will be apparent to one of ordinary skill in light of the following description of the invention and of the claims.

DETAILED DESCRIPTION OF THE INVENTION

In a first aspect, the invention provides a method of diagnosing a disease condition associated with the A allele (GA (SEQ ID NO:2) or AA (SEQ ID NO:3) genotype) at the −308 site of TNFα (SEQ ID NO:1). The first aspect of the invention further provides a method of identifying an animal, including a human, predisposed or susceptible to a risk associated with a particular genotype in a TNFα gene, said method comprising determining the genotype of said TNFα gene in said animal. In an embodiment of the invention, the method is to screen for an individual at risk of a condition or disease such as increased risk of death for patients with CAP by identifying the A allele (GA (SEQ ID NO:2) or AA (SEQ ID NO:3) genotype) in TNFα (SEQ ID NO:1) at −308.

The invention is based upon the observation reported herein of a correlation between the A allele (GA (SEQ ID NO:2) or AA (SEQ ID NO:3) genotype) in the TNFα gene (SEQ ID NO:1), specifically at position −308, and an increased risk of death in patients with CAP. The invention is of advantage in that by screening for the presence of the polymorphism it is possible to identify individuals likely to have a genetic predisposition or susceptibility to such increased risk. It may also result in substantially different management, especially prevention and treatment (vaccination), if CAP occurs, with subsequent substantial improvement in mortality and morbidity from CAP in this especially at risk population.

In an embodiment of the invention, diagnosis is carried out by determining whether a TNFα gene contains the GA or AA genotype at −308. Genotypic and allelic frequencies of this invention are readily determined by a number of methods known to those skilled in the art. Examples used in the present invention are shown in the Example below and include using PCR amplification and restriction enzyme digestion.

The method conveniently comprises amplifying a fragment of a TNFα gene to produce copies and determining whether copies of the fragment contain the particular genotype GA or AA.

Another suitable technique is to amplify the fragment using PCR techniques, producing copies of a fragment that is at least 500 base pairs in length, preferably at least 600 base pairs in length. It is preferred that the PCR primers are selected so as to amplify a region of the gene that is about 740 base pairs in length. PCR techniques are well known in the art and it would be within the ambit of a person of ordinary skill in this art to identify primers for amplifying a suitable section of the applicable exon of the TNFα gene. PCR techniques are described for example in EP-A-0200362 and EP-A-0201 184. In a further embodiment of the invention, the diagnostic method comprises analysis of the TNFα gene using single strand conformational polymorphism (SSCP) mapping to determine whether the TNFα gene is the risk or the non-risk form, i.e., the A allele at the −308 site.

As described above, in preferred embodiments of the first aspect of the invention, the method comprises screening a TNFα gene, and this screening is conveniently carried out by any one of a number of suitable techniques that are known in the art, and may be conveniently selected from amplification of a nucleic acid sequence located within the TNFα gene, Southern blotting of regions of the gene and single strand conformational polymorphism mapping of regions within the gene or as described in the example below. The genotype in that region is also optionally determined using a variety of methods including hybridization probes adapted selectively to hybridize with the particular polymorphism of the TNFα gene at the −308 location which is associated with predisposition or susceptibility to disease. A probe used for hybridization detection methods must be in some way labeled so as to enable detection of successfully hybridization events. This is optionally achieved by in vitro methods such as nick-translation, replacing nucleotides in the probe by radioactively labeled nucleotides, or by random primer extension, in which non-labeled molecules act as a template for the synthesis of labeled copies. Other standard method of labeling probes so as to detect hybridization are known to those skilled in the art.

According to a second aspect of the invention there is provided a method of diagnosis and therapy comprising diagnosing patients at increased risk of death with CAP according to the method of the first aspect of the invention and treating an individual having such increased risk by methods known to those of skill in the art such as pneumococcal and influenza vaccination and by using the novel treatment and prophylactic methods described below. It is preferable to do so prior to the patient having CAP. CAP can be diagnosed by methods known to those of skill in the art and as described herein.

Known therapies for CAP can be effective in halting advancement of the disease, or at least slowing the advancement. TNFα −308 gene analysis of this invention may also lead to more appropriate preventative measures, such as vaccination, and placement of patients into intensive care/critical care units, an important factor in optimizing survival from CAP. It is thus an advantage of the invention that early identification of patients at increased risk of death with CAP is improved, so that preventative therapy can be started as soon as possible, optimizing any interventions potential (such as immunomodulatory therapy) for affecting outcome. The decision of a physician on how and whether to initiate therapy in anticipation of the disease can be taken with increased confidence.

A variety of suitable treatments of patients at increased risk of death from CAP are described in the art and herein, and the contents of these are incorporated herein by reference. See also, Hirani and MacFarlane *Thorax* 1997.52:17–21, Pachon J. et al. *Am. Rev. Resp. Dis.* 1990.142:369–373, Ruiz M. et al. *Am. J. Respir. Crit. Care. Med.* 1999.160:923–929, Leeper and Torres *Clin. Chest. Med.* 1995.16:155–171. Other treatments will be known to persons of skill in the art.

A third aspect of the invention provides a composition for use in diagnosing a disease associated with a genetic polymorphism in a TNFα gene in an animal predisposed or susceptible to said increased risk of death, said composition comprising one or more primer nucleic acid molecules adapted to amplify a portion of a TNFα gene selected from a portion of the gene around the −308 location.

The composition of the third aspect of the invention may comprise a nucleic acid molecule capable of identifying the GA −308 genotype (or AA) in said TNFα gene, said genotype being indicative of a risk genotype in said animal.

A further embodiment of the third aspect of the invention provides a composition for identifying individuals at increased risk of death from CAP, comprising means for determining the genotype GA or AA of a TNFα gene of an individual at the −308 location such as the method provided in the example herein.

In an embodiment of the invention, a composition comprises PCR primers adapted to amplify a DNA sequence within and around the TNF −308 location, wherein alternative versions of the gene are distinguished one from another, i.e., whether or not the A allele is present.

In a further aspect of the invention there is provided a kit comprising a diagnostic composition such as described above and an indicator composition for indicating how possessing the GA or AA genotype of a TNFα −308 gene correlates with the increased risk of death in patients with CAP.

Diagnostic kits are typically accompanied by or comprise a chart or other visual aid for assistance in interpreting the results obtained using the kit. Suitable indicator compositions for use in the diagnostic kit of the invention include a leaflet or other visual reminder that possessing the risk polymorphism version of a TNFα gene (i.e., GA or AA genotype) correlates with increased risk of death in patients with CAP.

In a still further aspect of the invention there is provided use, in the manufacture of means for diagnosing whether an individual has an increased risk of death from CAP, of PCR primers adapted to amplify a region around −308 in the TNFα gene. Alternative versions of the gene are typically distinguished one from another by means known to those skilled in the art.

Multiple techniques exists and are known to one skilled in the art in the manufacture of means for diagnosing whether an individual has an increased risk of death from CAP by determining the GA or AA genotype (or A allele) of the gene TNFα at −308, for example, PCR primers adapted to amplify a region around −308 in the TNFα gene. One can use restriction analysis which generates different fragment lengths for the A allele (GA and GG genotype), identified by electrophoresis on an agarose gel where the different fragments migrate different amounts based on their size.

According to the invention, an individual who is heterozygous (GA) is classified as having an increased risk of death from CAP. Individuals with a AA genotype are believed to be at even higher risk.

Optionally, the assessment of an individual's risk factor according to any aspect of the invention is calculated by determining the genotype of a TNFα gene and combining the result with analysis of other known genetic or physiological or other risk factors known to those of skill in the art. The invention in this way provides further information on which measurement of an individual's risk can be based.

In another embodiment of the invention, the results of the genotyping done herein are used, along with other diagnostics measures and disease parameters, by treatment providers to determine the best course of treatment or prevention for the patient having been determined as susceptible to increased risk of death from CAP by the methods of this invention.

The TNFα polypeptide described in the present invention (A allele at the −308 site) may be beneficially employed in a screening process for compounds which stimulate (agonists) or inhibit (antagonists, or otherwise called inhibitors) the synthesis or action of the TNFα polypeptide. The TNFα polypeptide may also be employed in a screening process for compounds which mimic the agonist or antagonist properties of the TNFα polypeptide. Thus, the polypeptide encoded by TNFα (A allele at the −308 site) may also be used to assess and identify agonist or antagonists from, for example, cells, cell-free preparations, chemical libraries, and natural product mixtures. These agonists or antagonists may be natural substrates, ligands, receptors, etc., as the case may be, of the polypeptide of the present invention; or may be structural or functional mimetics of the polypeptide of the present invention. See Coligan et al., *Current Protocols in Immunology* 1(2):Chapter 5 (1991).

TNFα proteins are ubiquitous in the mammalian host and are responsible for many biological functions, including many pathologies. Accordingly, it is desirous to find compounds and drugs which stimulate TNFα polypeptide (A allele at −308) on the one hand and which can inhibit the function of TNFα polypeptide (A allele at −308) on the other hand.

In general, such screening procedures may involve identifying, generating and using appropriate cells which express the receptor of the TNFα polypeptide on the surface thereof. Such cells include cells from mammals, yeast, *Drosophila* or *E. coli*. Such cells may be identified, for example, by direct binding methods using radiolabeled or fluorescently tagged TNFα polypeptide (A allele at −308). Cells expressing the TNFα polypeptide receptor (or cell membrane containing the expressed polypeptide) are then contacted with a test compound to observe binding, or stimulation or inhibition of a functional response. Alternatively, the cDNA for the TNFα polypeptide receptor may be cloned by the above direct binding methods using expression cloning or purification methods known in the art, and its extracellular domain expressed as a secreted or membrane protein. The soluble or membrane bound receptor can then be used to identify agonists or antagonists via direct binding methods.

The assays may simply test binding of a candidate compound wherein adherence to the cells bearing the TNFα polypeptide receptor is detected by means of a label directly or indirectly associated with the candidate compound or in an assay involving competition with a labeled TNFα polypeptide. Further, these assays may test whether the candidate compound results in a signal similar to that generated by binding of the TNFα polypeptide, using detection systems appropriate to the cells bearing the TNFα polypeptide receptor at their surfaces. Inhibitors of activation are generally assayed in the presence of a known agonist and the effect on activation by the agonist by the presence of the candidate compound is observed. Standard methods for conducting such screening assays are well understood in the art.

Examples of potential TNFα polypeptide antagonists include antibodies or, in some cases, oligonucleotides or proteins which are closely related to the ligands, substrates, receptors, etc., as the case may be, of the TNFα polypeptide, e.g., a fragment of the ligands, substrates, receptors, or small molecules which bind to the target receptor of the present invention but do not elicit a response, so that the activity of the polypeptide is prevented. Preferred are those that can access and effect cellular function.

This invention provides methods of treating an abnormal conditions related to both an excess of and insufficient amounts of TNFα polypeptide (A allele) activity.

If the activity of TNFα polypeptide is in excess as is believed to be the case in the present invention, several approaches are available. One approach comprises administering to a subject an inhibitor compound (antagonist) as herein above described along with a pharmaceutically acceptable carrier in an amount effective to inhibit activation by blocking binding of the TNFα polypeptide to its target receptor, or by inhibiting a second signal, and thereby alleviating the abnormal condition, i.e., increased risk of death with CAP.

In another approach, soluble forms of TNFα polypeptides (A allele at −308) capable of binding its receptor in competition with endogenous TNFα polypeptide may be administered. Typical embodiments of such competitors comprise fragments of the TNFα polypeptide.

In still another approach, expression of the gene encoding endogenous TNFα polypeptide can be inhibited using expression blocking techniques. Known such techniques involve the use of antisense sequences, either internally generated or separately administered. See, for example, O'Connor, J. *Neurochem.* 1991.56:560 in Oligodeoxynucleotides as Antisense Inhibitors of Gene Expression, CRC Press, Boca Raton, Fla. (1988). Alternatively, oligonucleotides which form triple helices with the gene can be supplied. See, for example, Lee et al. *Nucleic Acids Res.* 1979.6:3073; Cooney et al. *Science* 1988.241:456; Dervan et al. *Science* 1991.251:1360. These oligomers can be administered per se or the relevant oligomers can be expressed in vivo.

For treating abnormal conditions related to an underexpression of TNFα and its activity, several approaches are also available. One approach comprises administering to a subject a therapeutically effective amount of the TNFα polypeptide or a compound, i.e., an agonist or mimetic as described above, in combination with a pharmaceutically acceptable carrier, to thereby alleviate the abnormal condition. Alternatively, gene therapy may be employed to effect the endogenous production of TNFα by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in *Human Molecular Genetics*, T. Strachan and A. P. Read, BIOS Scientific Publishers Ltd (1996).

All such agonists and antagonists are administered in an amounts effective to treat the condition and in pharmaceutically acceptable carriers. Techniques for determining effective amounts and carriers are well known to those of skill in the art.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following example, which is included herewith for purposes of illustration only and is not intended to be limiting of the invention.

EXAMPLE 1

Methods: Subjects were recruited as part of a prospective cohort study of patients with CAP. Septic shock was defined as a systolic blood pressure of <90 mmHg and at least 4 hours of inotropic support after adequate fluid replacement. Genotype was determined using PCR amplification and restriction enzyme digestion. The significance of trends was assessed using Fishers-exact test.

Results: 272 patients were successfully genotyped, 24 patients (8.8%) died, 28 (10.3%) had septic shock. 244 (89.7%) of patients were GG homozygotes, 27 GA (10.3%) heterozygotes and there were no AA homozygotes. Mortality was significantly higher in patients with GA or AA genotype (26% vs 7%, p=0.005, relative risk 3.7). There was no significant difference in the risk of septic shock (14.8% vs 9.8%, p=0.5). In a logistic regression model adjusting for age, sex, underlying cardiac failure, COPD and co-existing malignancy TNFα−308 GA remained an independent risk factor for death (p=0.02) with an adjusted odds ratio of 3.8.

Conclusion: TNFα −308 A allele (GA or AA genotype) carries a significantly greater risk of death from CAP, and may be an indication for pneumococcal and influenza vaccination.

What is claimed is:

1. A method of identifying a human patient at an increased risk of death from community-acquired pneumonia (CAP) associated with the A allele in a TNFα gene of SEQ ID NO:1 at the −308 locus, said method comprising determining the genotype at the −308 locus of said TNFα gene in said patient; and identifying increased risk of death from CAP based on said genotype.

* * * * *

SEQUENCE LISTING

<160> NUMBER OF SEQ ID NOS: 3

<210> SEQ ID NO 1
<211> LENGTH: 2088
<212> TYPE: DNA
<213> ORGANISM: Homo sapien

<400> SEQUENCE: 1
agttctatct ttttcctgca tcctgtctgg aagttagaag gaaacagacc acagacctgg    60
tccccaaaag aaatggaggc aataggtttt gaggggcatg gggacggggt tcagcctcca   120
gggtcctaca cacaaatcag tcagtggccc agaagacccc cctcggaatc ggagcaggga   180
ggatggggag tgtgaggggt atccttgatg cttgtgtgtc cccaactttc caaatccccg   240
cccccgcgat ggagaagaaa ccgagacaga aggtgcaggg cccactaccg cttcctccag   300
atgagctcat gggtttctcc accaaggaag ttttccgctg gttgaatgat tctttccccg   360

-continued

```
cctcctctc gccccaggga catataaagg cagttgttgg cacacccagc cagcagacgc      420
tccctcagca aggacagcag aggaccagct aagagggaga gaagcaacta cagacccccc      480
ctgaaaacaa ccctcagacg ccacatcccc tgacaagctg ccaggcaggt tctcttcctc      540
tcacatactg acccacggct ccaccctctc tccctggaa aggacaccat gagcactgaa       600
agcatgatcc gggacgtgga gctggccgag gaggcgctcc ccaagaagac aggggggccc      660
cagggctcca ggcggtgctt gttcctcagc ctcttctcct tcctgatcgt ggcaggcgcc      720
accacgctct tctgcctgct gcactttgga gtgatcggcc cccagaggga agagttcccc      780
agggacctct ctctaatcag ccctctggcc caggcagtca gatcatcttc tcgaaccccg      840
agtgacaagc tgtagcccca tgttgtagca accctcaag ctgaggggca gctccagtgg       900
ctgaaccgcc gggccaatgc cctcctggcc aatggcgtgg agctgagaga taaccagctg      960
gtggtgccat cagagggcct gtacctcatc tactcccagg tcctcttcaa gggccaaggc     1020
tgcccctcca cccatgtgct cctcacccac accatcagcc gcatcgccgt ctcctaccag     1080
accaaggtca acctcctctc tgccatcaag agccctgcc agaggagac cccagagggg       1140 gctgaggcca agccctggta tgagcccatc tatctgggag gggtcttcca gctggagaag     1200
ggtgaccgac tcagcgctga gatcaatcgg cccgactatc tcgactttgc cgagtctggg     1260
caggtctact ttgggatcat tgccctgtga ggaggacgaa catccaacct tcccaaacgc     1320
ctcccctgcc ccaatccctt tattacccc tccttcagac ccctcaacc tcttctggct       1380 caaaaagaga attgggggct tagggtcgga acccaagctt agaactttaa gcaacaagac     1440
caccacttcg aaacctggga ttcaggaatg tgtggcctgc acagtgaagt gctggcaacc     1500
actaagaatt caaactgggg cctccagaac tcactgggc ctacagcttt gatccctgac      1560
atctggaatc tggagaccag ggagcctttg gttctggcca gaatgctgca ggacttgaga     1620
agacctcacc tagaaattga cacaagtgga ccttaggcct cctctctcc agatgtttcc      1680 agacttcctt gagacacgga gcccagccct cccatggag ccagctccct ctatttatgt      1740
ttgcacttgt gattatttat tatttattta ttatttattt atttacagat gaatgtattt     1800
atttgggaga ccggggtatc ctgggggacc caatgtagga gctgccttgg ctcagacatg     1860
ttttccgtga aaacggagct gaacaatagg ctgttcccat gtagccccct ggcctctgtg     1920
ccttcttttg attatgtttt ttaaaatatt tatctgatta agttgtctaa acaatgctga     1980
tttggtgacc aactgtcact cattgctgag cctctgctcc ccaggggagt tgtgtctgta     2040
atcgccctac tattcagtgg cgagaaataa agtttgctta gaaaagaa                  2088
```

```
<210> SEQ ID NO 2
<211> LENGTH: 2088
<212> TYPE: DNA
<213> ORGANISM: Homo sapien

<400> SEQUENCE: 2
agttctatct ttttcctgca tcctgtctgg aagttagaag gaaacagacc acagacctgg       60
tccccaaaag aaatggaggc aataggtttt gagggggcatg aggacggggt tcagcctcca     120
gggtcctaca cacaaatcag tcagtggccc agaagacccc cctcggaatc ggagcaggga     180
ggatggggag tgtgagggt atccttgatg cttgtgtgtc cccaacttc caaatccccg       240 ccccgcgat ggagaagaaa ccgagacaga aggtgcaggg cccactaccg cttcctccag      300
atgagctcat gggtttctcc accaaggaag ttttccgctg gttgaatgat tctttccccg     360
```

|  |  |  |  |  |  |
|---|---|---|---|---|---|
| ccctcctctc | gccccaggga | catataaagg | cagttgttgg | cacacccagc | cagcagacgc | 420 |
| tccctcagca | aggacagcag | aggaccagct | aagagggaga | gaagcaacta | cagaccccc | 480 |
| ctgaaaacaa | ccctcagacg | ccacatcccc | tgacaagctg | ccaggcaggt | tctcttcctc | 540 |
| tcacatactg | acccacggct | ccaccctctc | tccctggaa | aggacaccat | gagcactgaa | 600 |
| agcatgatcc | gggacgtgga | gctggccgag | gaggcgctcc | caagaagac | agggggccc | 660 |
| cagggctcca | ggcggtgctt | gttcctcagc | ctcttctcct | tcctgatcgt | ggcaggcgcc | 720 |
| accacgctct | tctgcctgct | gcactttgga | gtgatcggcc | cccagaggga | agagttcccc | 780 |
| agggacctct | ctctaatcag | ccctctggcc | caggcagtca | gatcatcttc | tcgaaccccg | 840 |
| agtgacaagc | ctgtagccca | tgttgtagca | aaccctcaag | ctgaggggca | gctccagtgg | 900 |
| ctgaaccgcc | gggccaatgc | cctcctggcc | aatggcgtgg | agctgagaga | taaccagctg | 960 |
| gtggtgccat | cagagggcct | gtacctcatc | tactcccagg | tcctcttcaa | gggccaaggc | 1020 |
| tgccccttca | cccatgtgct | cctcacccac | accatcagcc | gcatcgccgt | ctcctaccag | 1080 |
| accaaggtca | acctcctctc | tgccatcaag | agccctgcc | agagggagac | cccagagggg | 1140 |
| gctgaggcca | agccctggta | tgagcccatc | tatctgggag | gggtcttcca | gctggagaag | 1200 |
| ggtgaccgac | tcagcgctga | gatcaatcgg | cccgactatc | tcgactttgc | cgagtctggg | 1260 |
| caggtctact | ttgggatcat | tgccctgtga | ggaggacgaa | catccaacct | tcccaaacgc | 1320 |
| ctcccctgcc | ccaatccctt | tattacccc | tccttcagac | accctcaacc | tcttctggct | 1380 |
| caaaaagaga | attgggggct | tagggtcgga | acccaagctt | agaactttaa | gcaacaagac | 1440 |
| caccacttcg | aaacctggga | ttcaggaatg | tgtggcctgc | acagtgaagt | gctggcaacc | 1500 |
| actaagaatt | caaactgggg | cctccagaac | tcactgggc | ctacagcttt | gatccctgac | 1560 |
| atctggaatc | tggagaccag | ggagcctttg | ttctggcca | gaatgctgca | ggacttgaga | 1620 |
| agacctcacc | tagaaattga | cacaagtgga | ccttaggcct | tcctctctcc | agatgttcc | 1680 |
| agacttcctt | gagacacgga | gcccagccct | cccccatggag | ccagctccct | ctatttatgt | 1740 |
| ttgcacttgt | gattatttat | tatttattta | ttatttattt | atttacagat | gaatgtattt | 1800 |
| atttgggaga | ccggggtatc | ctgggggacc | caatgtagga | gctgccttgg | ctcagacatg | 1860 |
| ttttccgtga | aaacggagct | gaacaatagg | ctgttcccat | gtagcccct | ggcctctgtg | 1920 |
| ccttctttg | attatgtttt | taaaatatt | tatctgatta | agttgtctaa | acaatgctga | 1980 |
| tttggtgacc | aactgtcact | cattgctgag | cctctgctcc | caggggagt | tgtgtctgta | 2040 |
| atcgccctac | tattcagtgg | cgagaaataa | agtttgctta | gaaaagaa |  | 2088 |

<210> SEQ ID NO 3
<211> LENGTH: 2088
<212> TYPE: DNA
<213> ORGANISM: Homo sapien

<400> SEQUENCE: 3

|  |  |  |  |  |  |
|---|---|---|---|---|---|
| agttctatct | ttttcctgca | tcctgtctgg | aagttagaag | gaaacagacc | acagacctgg | 60 |
| tccccaaaag | aaatggaggc | aataggtttt | gaggggcata | aggacggggt | tcagcctcca | 120 |
| gggtcctaca | cacaaatcag | tcagtggccc | agaagacccc | cctcggaatc | ggagcaggga | 180 |
| ggatggggag | tgtgagggt | atccttgatg | cttgtgtgtc | cccaactttc | caaatccccg | 240 |
| cccccgcgat | ggagaagaaa | ccgagacaga | aggtgcaggg | cccactaccg | cttcctccag | 300 |
| atgagctcat | gggtttctcc | accaaggaag | ttttccgctg | gttgaatgat | tctttccccg | 360 |
| ccctcctctc | gccccaggga | catataaagg | cagttgttgg | cacacccagc | cagcagacgc | 420 |

-continued

```
tccctcagca aggacagcag aggaccagct aagagggaga gaagcaacta cagaccccc     480
ctgaaaacaa ccctcagacg ccacatcccc tgacaagctg ccaggcaggt tctcttcctc     540
tcacatactg acccacggct ccaccctctc tccctggaa aggacaccat gagcactgaa      600
agcatgatcc gggacgtgga gctggccgag gaggcgctcc ccaagaagac aggggggccc    660
cagggctcca ggcggtgctt gttcctcagc ctcttctcct tcctgatcgt ggcaggcgcc     720
accacgctct tctgcctgct gcactttgga gtgatcggcc cccagaggga agagttcccc     780
agggacctct ctctaatcag ccctctggcc caggcagtca gatcatcttc tcgaaccccg    840
agtgacaagc ctgtagccca tgttgtagca aaccctcaag ctgaggggca gctccagtgg    900
ctgaaccgcc gggccaatgc cctcctggcc aatggcgtgg agctgagaga taaccagctg   960
gtggtgccat cagagggcct gtacctcatc tactcccagg tcctcttcaa gggccaaggc  1020
tgcccctcca cccatgtgct cctcacccac accatcagcc gcatcgccgt ctcctaccag  1080
accaaggtca acctcctctc tgccatcaag agccctgcc agagggagac cccagagggg   1140
gctgaggcca agccctggta tgagcccatc tatctgggag gggtcttcca gctggagaag  1200
ggtgaccgac tcagcgctga gatcaatcgg cccgactatc tcgactttgc cgagtctggg  1260
caggtctact ttgggatcat tgccctgtga ggaggacgaa catccaacct tcccaaacgc  1320
ctcccctgcc ccaatccctt tattacccc tccttcagac accctcaacc tcttctggct    1380
caaaagaga attgggggct tagggtcgga acccaagctt agaactttaa gcaacaagac   1440
caccacttcg aaacctggga ttcaggaatg tgtggcctgc acagtgaagt gctggcaacc  1500
actaagaatt caaactgggg cctccagaac tcactgggc ctacagcttt gatccctgac    1560
atctggaatc tggagaccag ggagcctttg gttctggcca gaatgctgca ggacttgaga  1620
agacctcacc tagaaattga cacaagtgga ccttaggcct tcctctctcc agatgtttcc  1680
agacttcctt gagacacgga gcccagccct cccatggag ccagctccct ctatttatgt    1740
ttgcacttgt gattatttat tatttattta ttatttattt atttacagat gaatgtattt  1800
atttgggaga ccggggtatc ctgggggacc caatgtagga gctgccttgg ctcagacatg  1860
ttttccgtga aaacggagct gaacaatagg ctgttcccat gtagccccct ggcctctgtg  1920
ccttcttttg attatgtttt ttaaaatatt tatctgatta agttgtctaa acaatgctga  1980
tttggtgacc aactgtcact cattgctgag cctctgctcc caggggagt tgtgtctgta    2040
atcgccctac tattcagtgg cgagaaataa agtttgctta gaaaagaa              2088
```